United States Patent [19]

Gleason et al.

[11] 4,387,239
[45] Jun. 7, 1983

[54] PROCESS FOR THE PREPARATION OF ESTERS OF LEUKOTRIENE A

[75] Inventors: John G. Gleason, Delran, N.J.; Charles M. Kinzig, Merion Station; Deborah L. Bryan, West Chester, both of Pa.

[73] Assignee: SmithKline Beckman Corporation, Philadelphia, Pa.

[21] Appl. No.: 333,850

[22] Filed: Dec. 22, 1981

Related U.S. Application Data

[62] Division of Ser. No. 230,915, Feb. 2, 1981, Pat. No. 4,352,757.

[51] Int. Cl.$^3$ .......................................... C07D 303/42
[52] U.S. Cl. .................................... 549/562; 549/548
[58] Field of Search ............................... 549/562, 548

[56] References Cited

PUBLICATIONS

Corey et al., Tetrahedron Letters, vol. 21, pp. 3463–3466, 4243–4246, (1980).
Baker et al., Tetrahedron Letters, vol. 21, pp. 4123–4126, (1980).
Hammarstrom et al., Biochem. Biophys. Res. Commun., vol. 92 (3), Feb. 12, 1980, pp. 946–953.
Corey et al., Jour. Am. Chem. Soc., vol. 102(4), Feb. 13, 1980, pp. 1436–1439.

*Primary Examiner*—Norma S. Milestone
*Attorney, Agent, or Firm*—Joseph F. DiPrima; Richard D. Foggio; Alan D. Lourie

[57] ABSTRACT

Esters of leukotriene A are conveniently prepared by reacting 9-oxo-5,6-trans-epoxynon-7(E)-enoates with 11-triphenylphosphoranylidene undec-6(Z),9(Z)-diene. Esters of leukotriene-A are useful intermediates in the synthesis of naturally occurring leukotrienes, which have been shown to be potent broncho-constricting substances. Novel intermediates to the esters of leukotriene A. 9-oxo-5,6-trans-epoxynon-7(E)-enoates and 7-oxo-5,6-trans-epoxyheptanoates, are disclosed.

2 Claims, No Drawings

PROCESS FOR THE PREPARATION OF ESTERS OF LEUKOTRIENE A

This is a divisional of application Ser. No. 230,915 filed Feb. 2, 1981, now U.S. Pat. No. 4,352,757.

BACKGROUND OF THE INVENTION

"Slow Reacting Substance of Anaphylaxis" (SRS-A) has been shown to be a highly potent broncho-constricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of cardiovascular effects of histamine.

The recent discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$, represented below as structural formula (LT-$C_4$) and leukotriene-$D_4$, represented below as structural formula (LT-$D_4$).

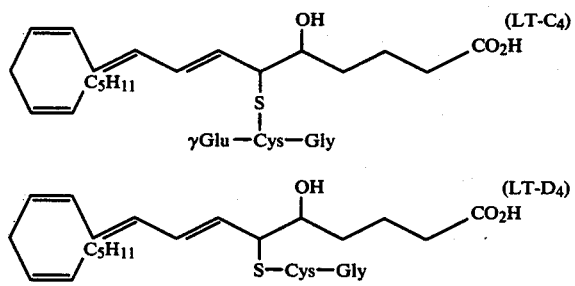

Leukotriene-A, represented below by the structural formula (LT-A), is believed to play a central role in natural conversion of arachidonic acid to the leukotrienes $C_4$ and $D_4$.

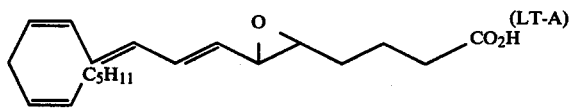

Leukotriene A has been converted to leukotrienes $C_4$ and $D_4$ via methods well known in the art. Synthetic leukotrienes have shown the same biological activities of their naturally occurring counterparts.

SUMMARY OF THE INVENTION

The esters of leukotriene A of this invention may be conveniently prepared by reacting 9-oxo-5,6-transepoxy-non-7(E)-enoate esters with 11-triphenylphosphoranylidene undec-6(Z),9(Z)-diene. This invention also relates to novel intermediates employed in the preparation of the esters of leukotriene A. These intermediates are 9-oxo-5,6-trans-epoxynon-7(E)-enoates and 7-oxo-5,6-transepoxyheptanoates.

DETAILED DESCRIPTION OF THE INVENTION

A process for the preparation of esters of leukotriene A, represented by the following structural formula (I):

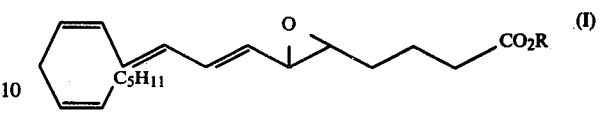

wherein R is alkyl of 1 to 4 carbon atoms, benzyl or 1,1,1,-trichloroethyl, comprises reacting 9-oxo-5,6-transepoxynon-7(E)-enoate ester, represented by the following structural formula (II):

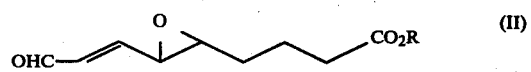

wherein R is defined above, with 11-triphenylphosphoranylidene undec-6(Z),9(Z)-diene, represented by the following structural formula (III):

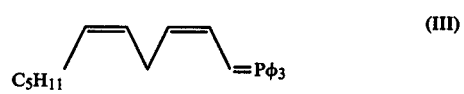

Particular alkyl esters of leukotrine A include those compounds of the formula (I) wherein R is ethyl, n-propyl, i-propyl, n-butyl, i-butyl, sec-butyl, tert-butyl and especially methyl.

The reaction of 9-oxo-5,6-trans-epoxynon-7(E)enoate ester with 11-triphenylphosphoranylidene undec-6(Z),9(Z)-diene is usually carried out at a temperature of about $-78°$ C. to about room temperature for from about 10 minutes to about 12 hours. The reaction is generally run in an aprotic organic solvent which is inert to the reactants under the reaction conditions. The addition of lithium iodide to the reaction mixture may increase the amount of the desired Z isomer about the $C_9$ double bond of the esters of leukotriene A prepared via the claimed process; however, even in the absence of lithium iodide the predominant stereoisomer obtained via the claimed process is the desired isomer.

The starting material 9-oxo-5,6-trans-epoxynon-7(E)-enoate ester of the formula (II) wherein R is alkyl of 1 to 4 carbon atoms, benzyl or 1,1,1,-trichloroethyl is conveniently prepared from 7-oxo-5,6-trans-epoxyheptanoate ester, represented by the following structural formula (IV):

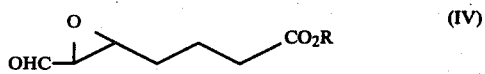

wherein R is defined above, and formylmethylenetriphenylphosphorane. This reaction is conducted under standard Wittig reaction conditions which are known to the skilled artisan.

In fact, the starting material 9-oxo-5,6-trans-epoxy-non-7(E)-enoate (II) may be prepared in three steps from 4-formylbutyrate derivatives via the following synthetic scheme:

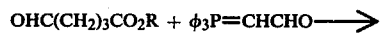

$OHC(CH_2)_3CO_2R + \phi_3P=CHCHO \longrightarrow$

-continued

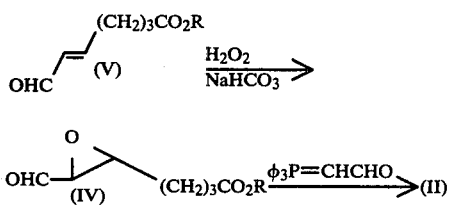

wherein R is described above.

The mixture of 4-formylbutyrate derivative and formylmethylenetriphenylphosphorne is refluxed in toluene to afford 7-oxo-hept-5(Z)-enoate (V). Epoxidation of the 7-oxo-hept-5(Z)-enoate (V) is carried out in basic media to give 7-oxo-5,6-transepoxyheptanoate (IV), which is converted to 9-oxo-5,6-trans-epoxynon-7(E)-enoate (II).

The starting material triphenylphosphoranylidene undec-6(Z),9(Z)-diene (III) is conveniently prepared from [undec-6(Z),9(Z)-diene]triphenylphosphonium halide, represented by the following structural formula (VI):

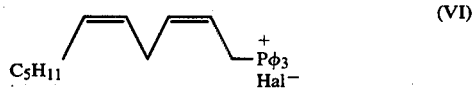

wherein Hal is bromide, chloride or iodide, in the presence of a non-nucleophilic base and an aprotic organic solvent. The conversion of the phosphonium halide (VI) to the phosphoranylidene (III) may be done in situ, that is the phosphoranylidene (III) may be formed in the reaction mixture prior or subsequent to the addition of the 9-oxo-5,6-trans-epoxynon-7(E)-enoate (II).

Examples of the non-nucleophilic bases which may be employed to convert the phosphonium halide (VI) to the phosphoranylidene (III) include n-butyllithium, methyllithium, tert.-butyllithium, lithium diisopropylamide and sodium hexamethylsilylamide [NaN(-Si(CH$_3$)$_3$)$_2$]. Illustrative of the aprotic organic solvents which may be present during this conversion are tetrahydrofuran, hexamethylphosphoramide, toluene and diethylether. The conversion is usually carried out at moderate to low temperatures, especially temperature at or below ambient temperatures.

In fact, the starting material triphenylphosphoranylidene undec-6(Z),9(Z)-diene (III) was prepared from oct-2-yne-1-ol via the following synthetic route:

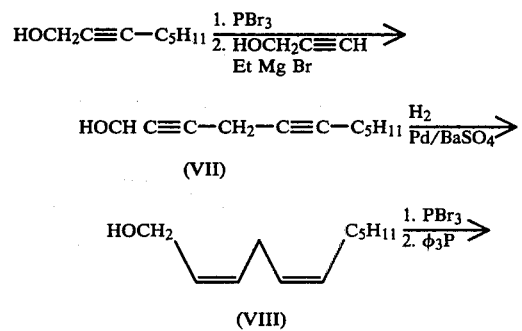

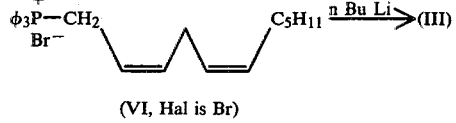

Oct-2-yne-1-ol was brominated with phosphorous tribromide and the resulting halide was coupled with dimagnesium halide salt of propargyl alcohol to yield the diynol (VII). Catalytic reduction of the diynol (VII) over palladium-barium sulfate catalyst afforded exclusively the Z,Z dienol (VIII) which was converted to the allylic bromide with phosphorous tribromide. The allylic bromide was reacted with triphenyl phosphine to give [undec-6(Z),9(Z)-diene]triphenylphosphonium bromide which was converted to triphenylphosphoranylidene undec-6(Z),9(Z)-diene (III).

The esters of leukotriene A prepared according to this invention may be employed as intermediates in the synthesis of the naturally occuring leukotrienes. The naturally occuring leukotrienes have been shown to be potent broncho-constricting substances and are useful as biological standards against which to test potential therapeutic agents.

The following examples illustrate the preparation of starting materials for the claimed process and the claimed process. As such, these examples are not to be considered as limiting the invention set forth in the claims appended hereto.

EXAMPLE I

Preparation of
Methyl-9-oxo-5,6-trans-epoxynon-7(E)-enoate
(Compound II, wherein R is methyl)

(a) Methyl-7-oxo-hept-5(Z)-enoate (V-R=CH$_3$)

A mixture of methyl-4-formylbutyrate (1.30 g, 10 mmol), formylmethylenetriphenylphosphorane (3.05 g, 10 mmol) and toluene (75 ml) was refluxed for 24 hours. The reaction mixture was concentrated at reduced pressure to remove toluene and hexane was added. The reaction mixture was then filtered and the filtrate concentrated at reduced pressure to yield the crude product. The crude product was distilled at reduced pressure to afford the desired material as a pale yellow oil (bp 64°–74° C. at 0.15 torr).

(b) Methyl-7-oxo-5,6-trans-epoxyheptanoate (IV, R=CH$_3$)

To a mechanical stirred solution of 30 percent hydrogen peroxide (8.24 ml, 1.1 equiv) in water (100 ml) and methanol (200 ml) with 1 N sodium bicarbonate (13.2 ml, 0.2 equiv) was added dropwise at ambient temperature over one hour methyl-7-oxo-hept-5(Z)enoate (10.31 g, 66 mmol) in methanol (100 ml). The pH of the reaction mixture was maintained between 9.25 and 9.5 by addition of 1 N sodium bicarbonate. The reaction mixture was heated to 40° C. and stirred for 3 hours. To the reaction mixture was added saturated aqueous ammonium sulfate solution (500 ml) and the methanol removed at reduced pressure. The resultant aqueous solution was extracted with methylene chloride and the extract dried over anhydrous magnesium sulfate. The resultant solution was chromatographed on silica gel eluting with 3% acetone/methylene chloride to afford the desired product as an oil.

| Analysis | C | H |
|---|---|---|
| Calculated | 55.81 | 7.02 |
| Found | 55.65 | 7.29 |

(C) Methyl-9-oxo-5,6-trans-epoxynon-7(E)enoate

A mixture of methyl-7-oxo-5,6-trans-epoxyheptanoate (4.8 g, 2.78 mmol), formylmethylenetriphenylphosphorane (8.93 g, 2.94 mmol) and toluene (400 ml) was heated to reflux for 5 hours and allowed to stand at ambient temperature for about 48 hours. The reaction mixture was concentrated at reduced pressure to remove toluene. The concentrate was triturated with diethyl ether and then chromatographed on silica gel eluting with 3% acetone/chloroform to afford a yellow oil.

| Analysis | C | H |
|---|---|---|
| Calculated | 60.59 | 7.12 |
| Found | 60.80 | 7.15 |

Satisfactory spectral data ($^1$H nmr, ms, ir and where appropriate $^{13}$C nmr) were obtained for all intermediates.

Similarly, the other 9-oxo-5,6-trans-epoxynon-7(E)-enoates of the instant invention may be prepared employing analogous starting materials under analogous reaction conditions.

EXAMPLE II

Preparation of triphenylphosphoranylidene undec-6(Z),9(Z)-diene (Compound III)

(a) Oct-2-yne-1-bromide

To a solution of oct-2-yn-1-ol (12 g, 96 mmol) in diethyl ether (40 ml) and pyridine (0.48 g, 6 mmol) was added dropwise at about −15° C. phosphorous tribromide (8.6 g, 32 mmol). The reaction mixture was allowed to warm to ambient temperature over 1.5 hours and heated to reflux for 30 minutes. The reaction mixture was then poured onto ice-sodium chloride mixture and the organic phase separated from the aqueous phase. The aqueous phase was extracted with diethyl ether. The combined organic phases were dried over anhydrous magnesium sulfate and then concentrated at reduced pressure to a slightly yellow liquid. The yellow liquid was distilled under reduced pressure to afford the desired product (bp 108°–118° C., 15 torr.)

(b) Undec-3,6-diyn-1-ol (VII)

To a slurry of magnesium metal (4.2 g, 175 mmol) in tetrahydrofuran (40 ml) at 0° C. over 30 minutes was added ethylbromide (21.2 g, 194 mmol) in tetrahydrofuran (20 ml). The mixture was stirred for an additional 30 minutes and propargyl alcohol (4.98 g, 89 mmol) in tetrahydrofuran (5 ml) was added over 30 minutes at 0° C. The resultant Grignard reagent was stirred at ambient temperature for 2 hours and then cooled to 0° C. Cuprous chloride (200 mg) was added and the mixture stirred for 20 minutes. To this mixture was added dropwise over 30 minutes oct-2-yn-1-bromide (10.5 g, 55 mmol) in tetrahydrofuran (15 ml). The reaction mixture was refluxed gently for 20 hours and an additional cuprous chloride (100 mg) was added. The reaction mixture was refluxed for an additional 5 hours, cooled to 0° C. and poured onto 2.5 N sulfuric acid (80 ml) and ice (100 ml). The resultant mixture was extracted with diethyl ether and the extract washed with 5% sodium carbonate and dried over anhydrous sodium sulfate. The resultant material was distilled at reduced pressure to afford the desired product as a yellowish liquid (bp 77°–96° 0.06–0.1 torr.)

(c) Undec-3(Z),6(Z)-dien-1-ol (VIII)

A slurry of 5% palladium-barium sulfate catalyst (115 mg) in hexane (20 ml) and quinoline (0.16 ml) is prehydrogenated at 35 psi of hydrogen in a Parr hydrogenation apparatus. Undec-3,6-diyn-1-ol (1.64 g, 10 mmol) was added to the prehydrogenated catalyst slurry and the resultant mixture hydrogenated for about 30 minutes. The resultant reaction mixture was filtered to remove the catalyst and the filtrate diluted with hexane. This solution was washed with 3 N hydrochloric acid, water and 5% sodium bicarbonate and dried over anhydrous sodium sulfate. The resultant material was chromatographed over silica gel and eluted with methylene chloride to yield the desired product. The stereochemistry of this product was confirmed by the use of Eu(fod)$_3$ shift reagent.

(d) 11-Bromo-undec-6(Z),9(Z)-diene

To a solution of undec-3(Z),6(Z)-dien-1-ol (100 mg, 0.6 mmol) in petroleum ether (5 ml) was added dropwise over 10 minutes at −20° C. phosphorous tribromide (275 mg, 10.1 mmol) in petroleum ether (3 ml). The reaction mixture was stirred for two hours at about −20° C., and one hour at room temperature and let stand for about 20 hours. The reaction mixture was then heated to reflux for 1½ hours, cooled and poured onto ice (30 ml) and 5% sodium bicarbonate (10 ml). The organic layer was separated and the aqueous layer extracted with diethyl ether. The combined organic phases were washed with 5% sodium carbonate, water and 1 N hydrochloric acid, dried over anhydrous sodium sulfate and filtered. The filtrate was concentrated at reduced pressure to afford the desired product.

(e) [Undec-6(Z),9(Z)-diene]triphenylphosphonium bromide (VI, Hal=Br)

To a solution of 11-bromo-undec-6(Z),9(Z)-diene (390 mg, 1.69 mmol) in toluene (4 ml) was added dropwise at 0° C. a solution of triphenylphosphine (1.8 g, 6.8 mmol) in toluene (4 ml). The reaction mixture is allowed to stand at 0° C. for about 20 hours and the reaction product precipitates out of solution. The reaction mixture is filtered and the filter cake washed with toluene and then dried in vacuo to yield the desired product (mp 140.5°–142° C.). Triphenylphosphoranylidene undec-6(Z),9(Z) diene is prepared by treating the above product with a non-nucleophilic base.

Satisfactory spectra data ($^1$H nmr, ms, ir and where appropriate $^{13}$C nmr) were obtained for all intermediates.

EXAMPLE III

Preparation of Methyl 5,6-oxido-7,9,11,14-eicosatetraenoate (Leukotriene A—methyl ester—Compound (I) R=CH$_3$)

(a) Triphenylphosphoranylidene-undec 6(Z),9(Z)-diene

To a slurry of [undec-6(Z),9(Z)-diene]triphenylphosphonium bromide (5.25 g, 10.6 mmol) in tetrahydrofuran (150 ml) under anhydrous conditions at −78° C.

was added dropwise n-butyllithium (4.6 ml-2.3 M). Upon the completion of the n-butyllithium addition the reaction mixture was warmed to −20° C. and stirred for 20 minutes to form the phosphoranylidene in solution.

(b) Leukotriene A—methyl ester from III(a)

To the phosphoranylidene formed according to III(a) at −78° C. was added dropwise over a few minutes methyl-9-oxo-5,6-trans-epoxynon-7(E)-enoate (2.61 g, 12.3 mmol) in tetrahydrofuran (15 ml). The reaction mixture was stirred for 10 minutes at −78° C., 20 minutes at −20° C. and 10 minutes at room temperature. The tetrahydrofuran was removed at reduced pressure and the residual oil is triturated with hexane. The hexane decantate is concentrated at reduced pressure, filtered and diluted to exactly 100 ml in hexane. Ultraviolet spectra indicates product obtained in good yield and purity.

(c) Leukotriene A methyl ester from phosphonium bromide II(e)

To a slurry of [undec-6(Z),9(Z)-diene]-triphenylphosphonium bromide (200 mg, 0.4 mmol) in tetrahydrofuran (3 ml) under anhydrous conditions at −78° C. was added dropwise n-butyllithium (165 μl, 0.4 mmol). The reaction mixture was stirred at −78° C. for 45 minutes and a small amount of the salt remains. To the reaction mixture was added at −78° C. was added dropwise methyl-9-oxo-5,6-trans-epoxynon-7(E)-enoate (103 mg, 0.49 mmol). The reaction mixture is stirred at −78° C. for 30 minutes and room temperature for 15 minutes. The tetrahydrofuran was removed at reduced pressure and the residual oil triturated with hexane. The hexane decantate is washed with water and dried over anhydrous sodium. The desired leukotriene A methyl ester was isolated as a pale yellow oil and was characterized as follows:

uv(hexane) 270s, 280, 290s; mass spectrum, m/e 332.2337 (calc'd for $C_{21}H_{32}O_3$, 332.2351); $^1H$ nmr (CDCl$_3$) 0.9 (t, C$_4$H$_8$C$\underline{H}_3$), 1.3 (m, (C$\underline{H}_2$)$_3$+C$\underline{H}_2$CH$_2$CO$_2$Me),

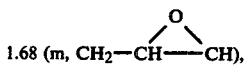

ca. 2.0 (m, C$\underline{H}_2$C=), 2.35 (broad t, C$\underline{H}_2$CO$_2$), 2.8

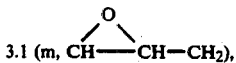

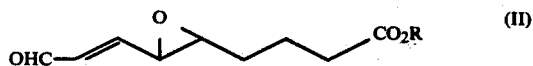

3.66 (s, OCH$_3$), 5.45 (m, CH$_2$—$\underline{H}$C=C$\underline{H}$—CH$_2$), ca. 6.3 (C$\underline{H}$=C$\underline{H}$); $^{13}$C nmr (CDCl$_3$)ppm 14.0 (C$_{20}$), 21.4 (C$_2$), 22.5 (C$_{19}$), 26. (C$_{17}$), 27.3, 28.0 (C$_{13}$), 29.3 (C$_{17}$), 31.3, 31.5 (C$_{18}$, C$_3$), 33.6 (C$_4$) 51.5 (CH$_3$O), 58.3 (C$_6$), 60.5 (C$_5$), 174 (C$_1$), 124–135 (vinyl). The complexity of the vinyl region as well as the observation of doublets in the $^{13}$C spectrum for both C$_{13}$ and C$_6$ suggests that the final product was a mixture of E and Z isomers about the C$_9$ double bond.

What is claimed is:

1. A compound represented by the following structural formula (II):

OHC—/=\—O—/\—/\—CO$_2$R (II)

wherein R is alkyl of 1 to 4 carbon atoms, benzyl or 1,1,1-trichloroethyl.

2. A compound according to claim 1 which is methyl-9-oxo-5,6-trans-epoxynon-7(E)-enoate.

* * * * *